United States Patent [19]
Steen

[11] Patent Number: 6,142,149
[45] Date of Patent: Nov. 7, 2000

[54] OXIMETRY DEVICE, OPEN OXYGEN DELIVERY SYSTEM OXIMETRY DEVICE AND METHOD OF CONTROLLING OXYGEN SATURATION

[76] Inventor: Scot Kenneth Steen, 2254 Sierra Ladera, Bishop, Calif. 93514

[21] Appl. No.: 09/164,410

[22] Filed: Sep. 30, 1998

Related U.S. Application Data

[60] Provisional application No. 60/062,885, Oct. 23, 1997.

[51] Int. Cl.$^7$ ..................................................... A61M 16/00
[52] U.S. Cl. ................................. 128/204.23; 128/204.21
[58] Field of Search ........................ 128/204.21, 204.23, 128/205.11, 202.22, 205.23

[56] References Cited

U.S. PATENT DOCUMENTS

| | | |
|---|---|---|
| 3,734,091 | 5/1973 | Taplin . |
| 4,401,431 | 8/1983 | Arp .............................................. 604/4 |
| 4,584,996 | 4/1986 | Blum ................................... 128/204.21 |
| 4,593,248 | 6/1986 | Hyde et al. ............................... 324/317 |
| 4,648,395 | 3/1987 | Sato et al. ............................ 128/204.23 |
| 4,825,879 | 5/1989 | Tan et al. .................................. 128/633 |
| 4,874,581 | 10/1989 | Sutherland et al. ....................... 422/46 |
| 4,889,116 | 12/1989 | Taube .................................. 128/204.23 |
| 4,938,218 | 7/1990 | Goodman et al. ........................ 128/633 |
| 5,061,632 | 10/1991 | Shepherd et al. ........................... 436/66 |
| 5,076,271 | 12/1991 | Lekholm et al. ................. 128/419 PG |
| 5,315,990 | 5/1994 | Mondry ............................... 128/204.23 |
| 5,323,776 | 6/1994 | Blakeley et al. .......................... 128/633 |
| 5,363,842 | 11/1994 | Mishelevich et al. .............. 128/200.14 |
| 5,365,922 | 11/1994 | Raemer ................................ 128/204.23 |
| 5,388,575 | 2/1995 | Taube .................................. 128/204.23 |
| 5,528,365 | 6/1996 | Gonatas ................................... 356/340 |
| 5,558,086 | 9/1996 | Smith et al. ......................... 128/204.26 |
| 5,603,315 | 2/1997 | Sasso, Jr. ............................ 128/204.18 |
| 5,682,877 | 11/1997 | Mondry .............................. 128/205.11 |
| 5,931,160 | 8/1999 | Gilmore et al. .................... 128/204.21 |

FOREIGN PATENT DOCUMENTS

| | | |
|---|---|---|
| 0 249 308 A2 | 12/1987 | European Pat. Off. . |
| 0 303 502 A1 | 2/1989 | European Pat. Off. . |

*Primary Examiner*—Aaron J. Lewis
*Attorney, Agent, or Firm*—Wells, St. John, Roberts, Gregory & Matkin, P.S.

[57] ABSTRACT

The present invention includes oximetry devices, open oxygen delivery system oximetry devices and method for controlling oxygen saturation. According to one aspect of the present invention, an oximetry device includes: an oxygen saturation sensor adapted to couple with an individual and configured to provide oxygen saturation information of the individual; an oxygen flow sensor adapted to couple with an oxygen source and configured to provide flow rate information of supplemental oxygen delivered to the individual; a controller coupled with the oxygen saturation sensor and adapted to control a flow valve to control the flow rate of supplemental oxygen delivered to the individual responsive to the oxygen saturation information provided by the oxygen saturation sensor; and a memory device coupled with the controller and configured to store the oxygen saturation information and flow rate information of supplemental oxygen.

20 Claims, 6 Drawing Sheets

OXIMETRY DEVICE, OPEN OXYGEN DELIVERY SYSTEM OXIMETRY DEVICE AND METHOD OF CONTROLLING OXYGEN SATURATION

CROSS REFERENCE TO RELATED APPLICATIONS

This application claims priority from U.S. Provisional application 60/062,885, filed Oct. 23, 1997, titled "Programmable Flow Controller", and incorporated herein by reference.

TECHNICAL FIELD

The present invention relates to an oximetry device, open oxygen delivery system oximetry device and method for controlling oxygen saturation.

BACKGROUND OF THE INVENTION

Patients with severely compromised respiratory systems are typically unable to maintain an adequate oxygen saturation (also referred to as saturation per pulse oximetry or $SpO_2$) without the use of supplemental oxygen. The respiratory systems of these individuals may be damaged due to disease or other complications. The lungs of such patients are not able to sufficiently receive oxygen and discharge carbon dioxide ($CO_2$). As a result, individuals with these complications may have periods when the level of oxygen saturation in the blood is very low, due to exertion, and other moments in time when the level can rise to a near critical level due to lack of exertion.

Currently in the medical community doctors typically request an arterial blood gas test to determine the amount of oxygen and $CO_2$ in the patient's blood. Thereafter, the doctor is able to prescribe supplemental oxygen flow levels for the patient based upon the determined values. A physician can prescribe an increase in the fractional inspired oxygen ($FiO_2$) through the use of supplemental oxygen. The body equilibrates a change in fractional inspired oxygen in approximately 15 to 20 minutes in an average case. Supplemental flow levels are chosen to preferably maintain the patient within a predefined $SpO_2$ range and not create a high level of carbon dioxide. High levels of either oxygen or carbon dioxide can be very detrimental to such patients.

Typically, patients with compromised respiratory systems are rechecked using a pulse oximeter to obtain the patient's $SpO_2$. The readings for particular individuals are typically performed on a scheduled basis in a health care facility. The basis may be monthly or even weekly for outpatients. This monitoring is performed to assure that the oxygen saturation is within a prescribed range.

Conventional treatment methods have a variety of drawbacks. The necessary monitoring of the oxygen level is at least an inconvenience for individuals having compromised respiratory systems. Further, such monitoring provides only a snapshot of the patient's oxygen saturation level over a given period of time. The physician is not provided with numerous data points which could possibly be utilized to assist with prescribing more helpful treatment for an individual. Although the fractional inspired oxygen and oxygen saturation levels can be increased through the use of supplemental oxygen, some associated problems of numerous individuals are not cured through the use of supplemental oxygen at one prescribed level. For example, during periods of exertion the individual may need more supplemental oxygen than the prescribed level. On the other hand, complications can result if the prescribed level of supplemental oxygen is too high.

Therefore, there exists a need in the art to provide improved devices and methods of determining oxygen saturation levels of individuals with compromised respiratory systems as well as delivering supplemental oxygen to such individuals.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

One use of the present invention is to aid patients having compromised respiratory systems. Such people typically require supplemental oxygen. However, other uses of the present invention are possible. For example, the oximetry device according to the present invention may be utilized in a high-altitude work environment, high-altitude flight, underwater exploration, or in any other application where it is desired to control the flow of oxygen.

The devices and methods of the present invention are configured to control the flow of supplemental oxygen delivered to a patient to maintain their $SpO_2$ within a prescribed range. In general, the device is configured in one embodiment to receive $SpO_2$ data from a pulse oximetry unit. Such data is typically a 0–5 volt DC output. The oximetry device of the present invention is configured to compare the data with a $SpO_2$ range which is preset in memory. If the $SpO_2$ is not within the desired range, the device is configured to adjust the amount of oxygen delivered to the patient inversely to the $SpO_2$ deviation. The amount of deviation will in part dictate the degree of change in the supplemental oxygen flow in the described embodiment. Prior to any change in the oxygen flow, it is preferred to compare the desired flow rate to preset minimum and maximum flow rates to assure that neither will be exceeded by the desired change.

According to one aspect of the present invention, an oximetry device comprises: an oxygen saturation sensor adapted to couple with an individual and configured to provide oxygen saturation information of the individual; an oxygen flow sensor adapted to couple with an oxygen source and configured to provide flow rate information of supplemental oxygen being delivered to the individual; a controller coupled with the oxygen saturation sensor and adapted to control a flow valve to control the flow rate of supplemental oxygen delivered to the individual responsive to the oxygen saturation information provided by the oxygen saturation sensor; and a memory device coupled with the controller, the memory device being configured to store the oxygen saturation information and the corresponding flow rate information of supplemental oxygen.

According to a second aspect of the present invention, an open oxygen delivery system oximetry device comprises: an oxygen saturation sensor adapted to couple with an individual and provide oxygen saturation information of the individual; an oxygen flow sensor adapted to couple with an oxygen source and provide flow rate information of supplemental oxygen delivered to the individual; a controller coupled with the oxygen saturation sensor and the oxygen flow sensor, the controller being adapted to control a flow valve to control the quantity of oxygen being delivered to the individual responsive to oxygen saturation information provided by the oxygen saturation sensor, the controller being further configured to selectively control the flow valve to deliver oxygen to the individual at a predefined intermediate default rate; a memory device coupled with the controller, the memory device being configured to store a history including the oxygen saturation information comprising a plurality of saturation levels measured over a period of time and the flow rate information comprising a plurality of supplemental oxygen flow rate values corresponding to the respective oxygen saturation levels; and an interface coupled with the memory and adapted to couple with an external data device, the interface being configured to communicate the history to the external data device and receive a desired oxygen saturation range from the external data device.

According to another aspect of the present invention, an oxygen saturation control method comprises: providing an oxygen source; coupling an individual with the oxygen source; obtaining oxygen saturation information of the individual; selectively delivering a quantity of supplemental oxygen at a flow rate to the individual from the oxygen source responsive to monitoring; and storing the oxygen saturation information of the individual and flow rate information of the supplemental oxygen delivered to the individual.

Figure 1:
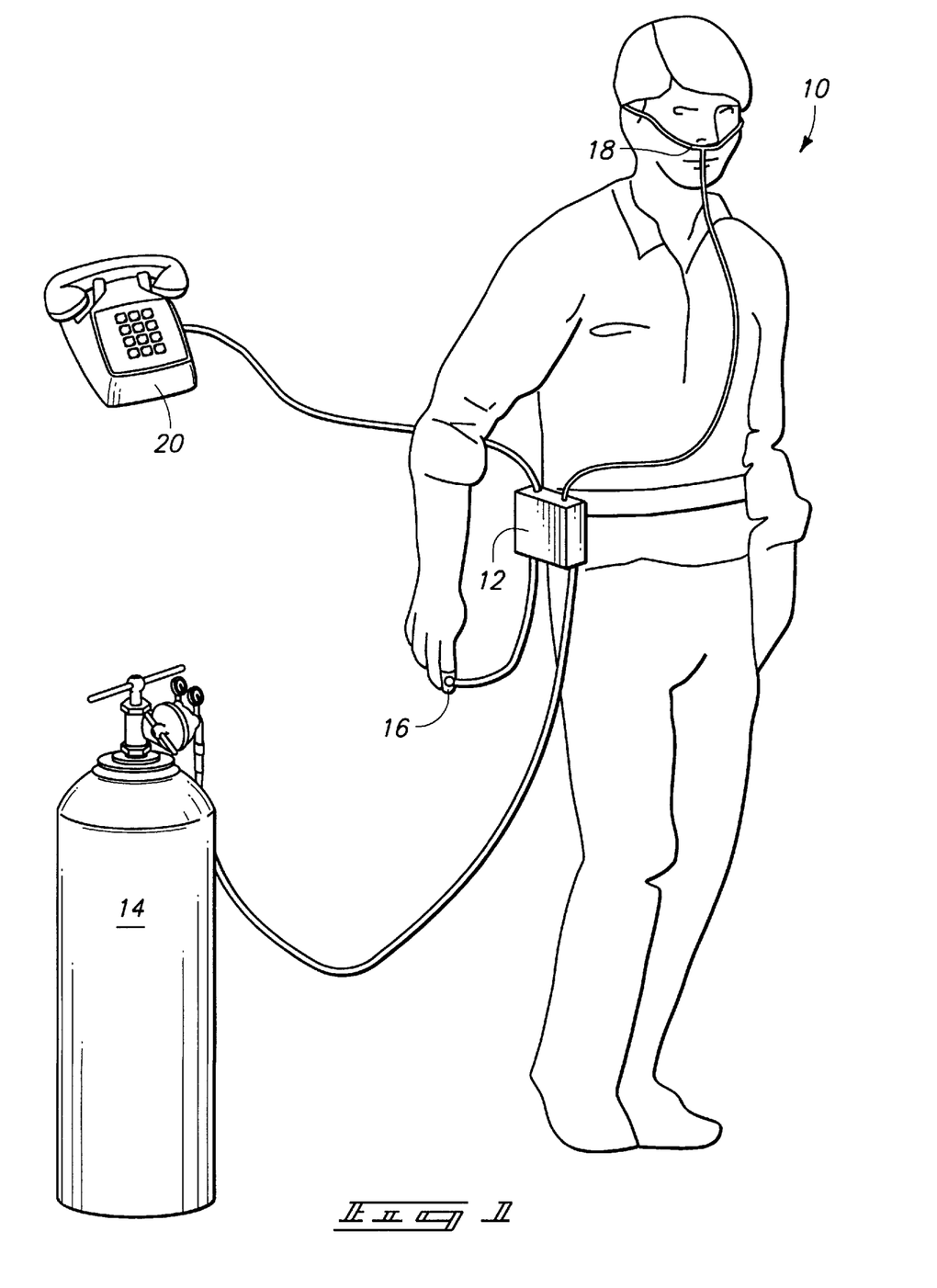
FIG. 1 is an illustrative representation of an individual utilizing an oximetry device in accordance with the present invention.

Referring to FIG. 1, an individual 10 is shown utilizing an oximetry device 12 according to the present invention. The illustrated oximetry device 12 is coupled with an oxygen source 14, oxygen saturation sensor 16, delivery apparatus 18, and telephone 20. Oxygen source 14 comprises a pressurized tank in the depicted embodiment. Oxygen source 14 is preferably configured for portable use in a preferred embodiment.

Oxygen saturation sensor 16 is adapted to couple with individual 10 and provide oxygen saturation (i.e., $SpO_2$) information of the individual. In one embodiment, oxygen saturation sensor 16 comprises an oximeter for attachment to a finger of individual 10. Other oxygen saturation sensor configurations can be utilized. Oxygen saturation sensor 16 is configured to output oxygen saturation levels of individual 10 to oximetry device 12.

Oxygen delivery apparatus 18 comprises a nasal cannula coupled with oximetry device 12. Oximetry device 12 is configured for use in an open delivery system in the described embodiment. Other configurations of delivery apparatus 18 are possible. Delivery apparatus 18 is operable to provide supplemental oxygen to individual 10 to increase the fractional inspired oxygen received by individual 10.

As shown, oximetry device 12 is also configured to couple with a telephone 20 in the depicted illustration. Data generated by oximetry device 12 can be applied to telephone 20 for transmission to a remote location such as a physician's office or other data bank. In addition, oximetry device 12 may be configured to receive configuration data or other information from a remote location utilizing telephone 20. Other communication media configurations to provide remote communications are possible in other embodiments.

Figure 2:
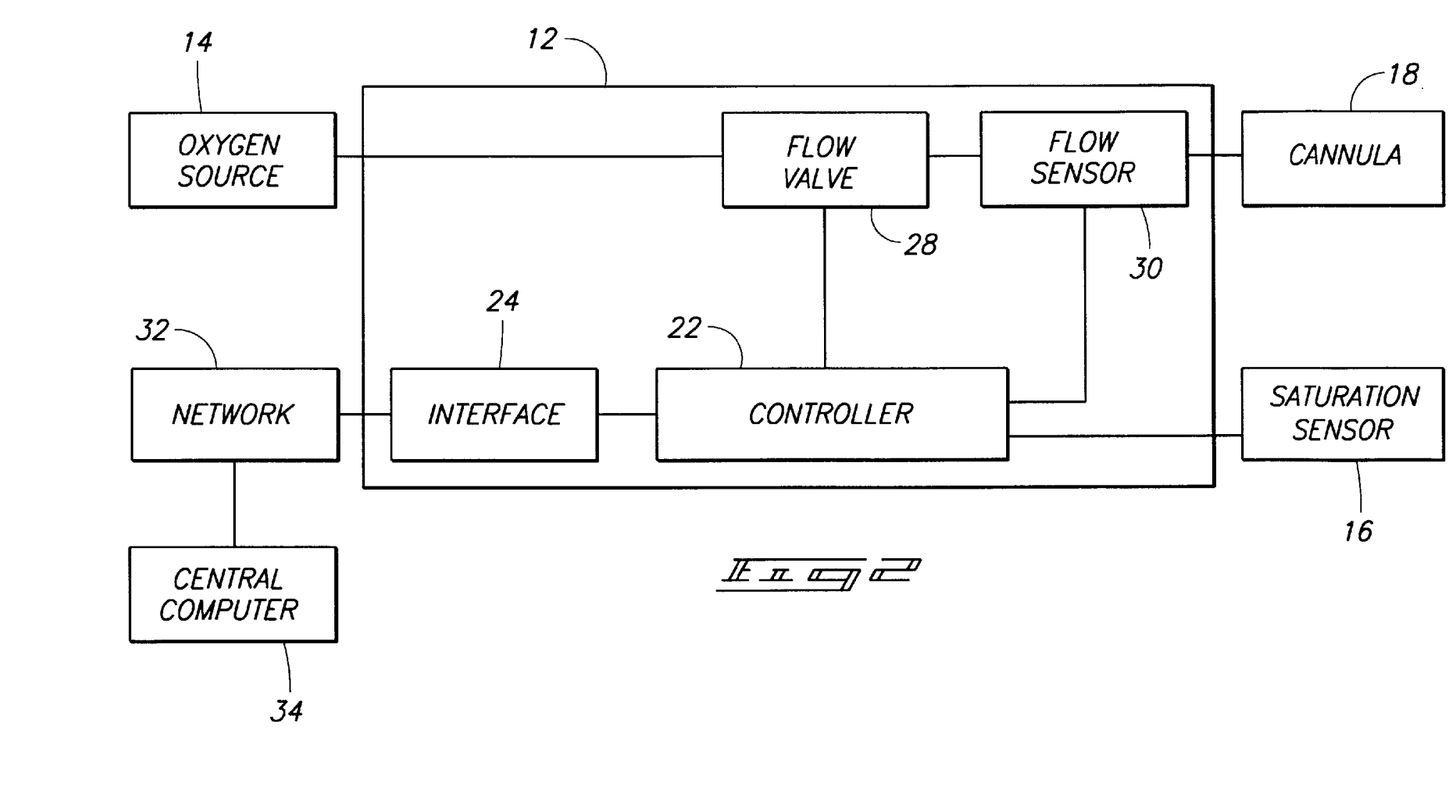
FIG. 2 is a functional block diagram of one embodiment of an oximetry device.

Referring to FIG. 2, internal components of one embodiment of oximetry device 12 are illustrated. The depicted oximetry device 12 comprises a controller 22, interface 24, control valve 28, and flow sensor 30. Controller 22 preferably includes an internal memory described below.

As shown, flow valve 28 is configured to couple with oxygen source 14. As described below, supplemental oxygen is received within oximetry device 12 from oxygen source 14 and applied to flow valve 28. Responsive to control from controller 22, flow valve 28 adjusts the amount of supplemental oxygen delivered to individual 10 via delivery apparatus or cannula 18. Oximetry device 12 is preferably configured to adjust the flow of supplemental oxygen from source 14 inversely to the relationship of the oxygen saturation level of individual 10. For example, if the oxygen saturation of individual 10 falls below a desired oxygen saturation range, oximetry device 12 is configured to increase the flow of supplemental oxygen from source 14 to individual 10. Alternatively, if the oxygen saturation level of individual 10 rises above a desired oxygen saturation range, oximetry device 12 is configured to decrease the flow of supplemental oxygen from source 14 to individual 10.

Flow sensor 30 is configured to provide information regarding the flow of supplemental oxygen to individual 10. Typically such flow of oxygen is provided within a predefined range which is zero to six liters per minute in an exemplary embodiment. A physician preferably prescribes minimum and maximum flow rates of supplemental oxygen.

Controller 22 is configured to receive information from flow sensor 30 and control the operation of valve 28 responsive thereto. Oxygen flow sensor 30 is adapted to couple with oxygen source 14 via control valve 28 and provide information of a quantity of oxygen being delivered to individual 10. Controller 22 is coupled with oxygen saturation sensor 16 and adapted to control flow valve 28 to control the quantity of oxygen delivered to individual 10 responsive to oxygen saturation information provided by oxygen saturation sensor 16. In one embodiment, controller 22 comprises an application specific integrated circuit (ASIC).

Figure 3:
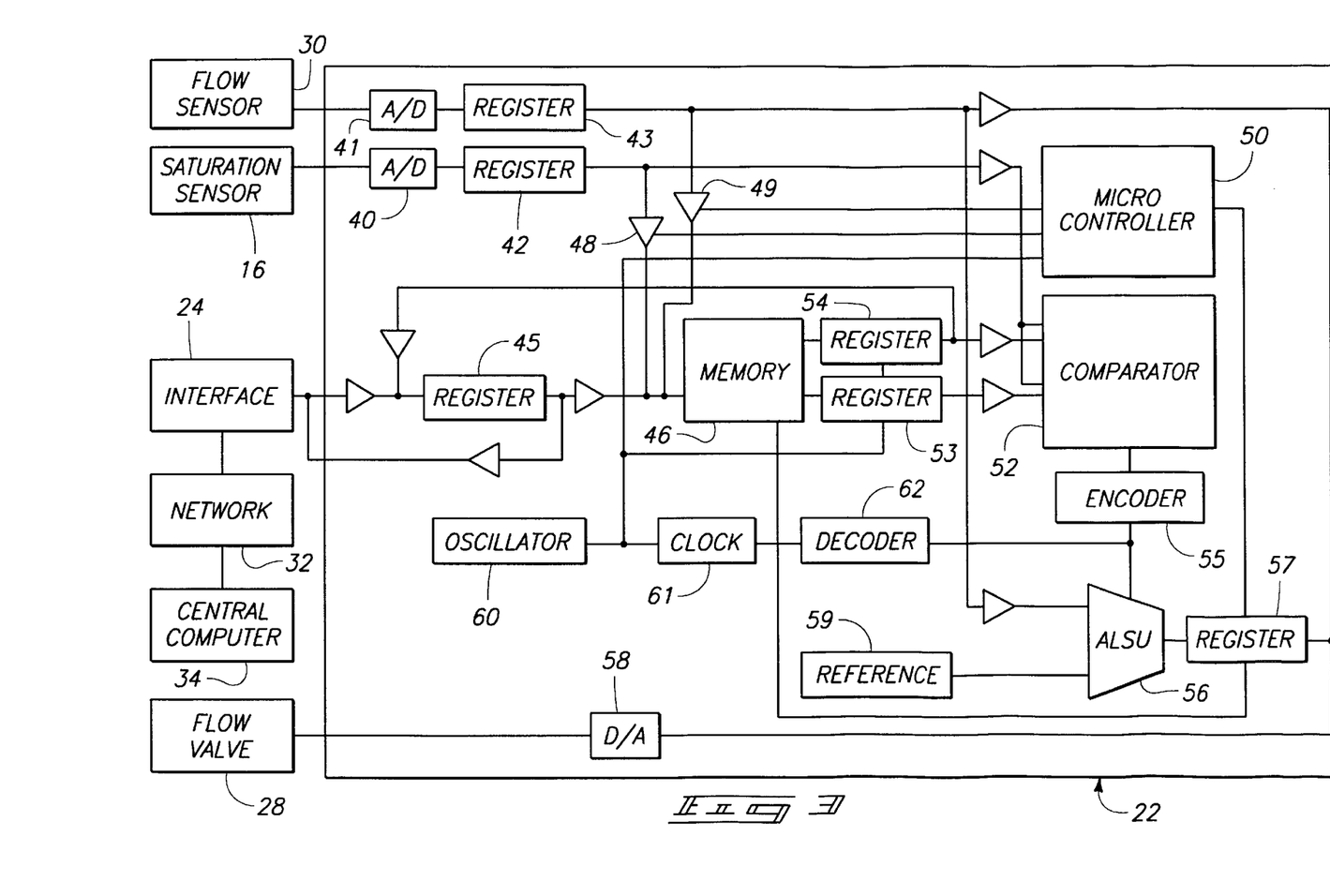
FIG. 3 is a functional block diagram of a controller of the oximetry device.

The internal memory device of controller 22 is depicted in FIG. 3 as reference number 46. Memory device 46 is configured to store oxygen saturation information provided from saturation sensor 16 and the corresponding quantity of supplemental oxygen information delivered to individual 10 from source 14.

Memory device 46 is configured in a preferred embodiment to store a history including oxygen saturation information comprising a plurality of oxygen saturation levels measured over a period of time and quantity of oxygen information comprising a plurality of supplemental oxygen flow values corresponding to the respective saturation values.

The embodiment of oximetry device 12 described herein further comprises an interface 24 coupled with memory of controller 22. Interface 24 is adapted to couple with an external network 32 and central computer 34. Interface 24 is configured to communicate oxygen saturation information and corresponding quantity of supplemental oxygen information to central computer 34 using external network 32. An external data device comprising central computer 34 may be a physician's computer or a hospital database in one embodiment. Such permit s a physician to remotely monitor the condition of individual 10. In preferred embodiments, oximetry device 12 is configured to communicate a history stored within the memory using interface 24 to network 32 and central computer 34.

In another application, a physician can utilize central computer 34 and network 32 to communicate information or settings to oximetry device 12 using interface 24. Such information can comprise minimum and maximum oxygen saturation levels and minimum and maximum supplemental oxygen flow values. Controller 22 is configured to store received information within the memory for further operation of oximetry device 12.

In one embodiment, network 32 comprises a packet switched network such as the Internet, or an internal network such as a local area network present in a hospital. Network 32 can also comprise a public switched telephone network (PSTN). Other network configurations are possible. Interface 24 is configured to communicate via the provided network 32. In such configurations, interface 24 is preferably configured to provide bi-directional communications via network 32.

Oximetry device 12 is preferably configured to deliver a preset default minimum supplemental oxygen flow to delivery apparatus 18 in the event of system failure or other prescribed event. Such a preset default minimum oxygen flow could be two liters per minute (LPM). Exemplary system failures could include a power failure wherein any provided battery backup fails, no data is received from saturation sensor 16, received data for sensor 16 is unreliable, or any other condition.

In the event of system failure, controller 22 instructs flow valve 28 to present a supplemental oxygen flow rate to patient 10 at a predetermined fail-safe default flow rate. The default flow is preferably prescribed by the physician. The physician could preferably adjust the default rate corresponding to the particular individual 10 being treated.

Further, responsive to the history stored within memory 46 regarding the particular individual 10, a physician can additionally remotely adjust the default value utilizing central computer 34 and network 32 in one application of oximetry device 12. As such, controller 22 is configured to selectively deliver supplemental oxygen to individual 10 at a predefined intermediate default rate.

Supplemental oxygen flow may be maintained by a failsafe solenoid within oximetry device 12 which is mechanically operated and automatically activated upon loss of power. Such could be utilized to supply the default flow rate of supplemental oxygen responsive to the failure of controller 22, no received signal from sensor 16, or no received signal from microcontroller 50.

Referring to FIG. 3, one embodiment of controller 22 is illustrated in detail. Controller 22 is coupled with saturation sensor 16, flow valve 28, flow sensor 30, network 32, and central computer 34. Saturation sensor 16 is operable to provide a signal corresponding to the amount of saturated oxygen in the blood of individual 10. Flow sensor 30 is operable to provide a signal corresponding to the amount of supplemental oxygen being delivered to individual 10.

The signals outputted from saturation sensor 16 and flow sensor 30 comprise analog signals in the preferred embodiment. Such signals are applied to respective analog to digital converters 40, 41 wherein such signals are converted to digital signals. The digitized signals are applied to respective registers 42, 43 wherein the signals are temporarily stored.

Interface 24 couples network 32 and central computer 34 with controller 22. In particular, interface 24 is coupled with an internal register 45 of controller 22. Register 45 is configured to temporarily store inputted and/or outputted data. As described in detail below, such inputted data can comprise oxygen saturation range levels including a minimum oxygen saturation level and a maximum oxygen saturation level, minimum and maximum supplemental oxygen flow rates and a default supplemental oxygen flow level as prescribed by the physician. The physician can further program minimum and maximum supplemental oxygen flow rates.

Exemplary output data to be applied to central computer 34 from register 45 comprises history information corresponding to the individual's oxygen saturation levels and respective supplemental oxygen flow levels over a period of time.

Register 45 is coupled with memory 46 which is configured to store the inputted and outputted data. In the described configuration, memory 46 comprises nonvolatile memory.

Plural tri-state buffers 48, 49 are coupled with respective registers 42, 43 and memory 46. Microcontroller 50 is configured to operate tristate buffers 58, 59 and control the reading and writing of data from and to memory 46. Responsive to selective control from microcontroller 50, tri-state buffers 48, 49 selectively pass input data received from respective saturation sensor 16 and flow sensor 30 into memory 46 to create a history log. Microcontroller 50 can be programmed to allow such data to pass into memory 46 at selected time intervals such as every half hour, hour or other interval. Additionally, microcontroller 50 can be programmed to store data within memory 46 responsive to the individual having an oxygen saturation level outside of a desired oxygen saturation range.

Controller 22 additionally comprises a comparator 52 configured to compare the current oxygen saturation level reading provided by saturation sensor 16 with the oxygen saturation range levels prescribed by the physician. Comparator 52 is coupled with register 42 containing oxygen saturation information and with memory 46 via registers 53, 54 to receive the oxygen saturation range levels comprising minimum and maximum oxygen saturation levels prescribed by the physician. Comparator 52 determines whether the measured oxygen saturation level is within the prescribed range.

Comparator 52 is coupled with an encoder 55 and an arithmetic logic shift unit (ALSU) 56. ALSU 56 is configured to provide an adjustment of supplemental oxygen delivered to individual 10 responsive to the comparison of the individual's oxygen saturation level and the prescribed range.

In one embodiment, encoder 55 observes the results from comparator 52 and controls arithmetic shift logic unit 56. In particular, encoder 55 instructs arithmetic shift logic unit 56 to either increase or decrease supplemental oxygen flow. ALSU 56 is configured to adjust the rate of oxygen delivered to individual 10 by 0.5 liters per minute in either increase flows or decrease flows. More specifically, ALSU is coupled with a reference 59 to provide a predefined increment or decrement of the supplemental oxygen flow level. In the preferred embodiment, reference 59 is chosen to provide a increase or decrease increment of 0.5 liters per minute.

ALSU 56 is coupled with a register 57 and a digital to analog converter 58 to provide control operations of control valve 28. ALSU 56 operates to output a increment or decrement signal to register 57 for combination with a signal received from flow sensor 30 for adjusting flow valve 28.

Controller 22 additionally comprises an oscillator 60, clock 61 and decoder 62. Oscillator 60 is configured to output a reference signal at a predefined frequency. Clock 61 comprises a real time cell module in the described embodiment. Decoder 62 receives the output from clock 61 and can instruct arithmetic logic shift unit 56 when to adjust the control signal applied to flow valve 28 in combination with the output with comparator 52. Utilization of register 57 enables proper timing of the output of the adjusted signal for controlling flow valve 28.

An appropriate power supply is utilized to power various components of oximetry device 12. Such could comprise a nickel—cadmium battery utilized in combination with solar cells. Such solar cells could be utilized to power oximetry device 12 during daytime hours while simultaneously powering the nickel-cadmium battery. Accordingly, the nickel-cadmium battery could be utilized to power the oximetry device 12 at night or during failure of the solar cells. Other power supplies can be utilized. Flow valve 28 is preferably configured to default to a predefined position to provide an intermediate default flow of supplemental oxygen from oxygen source 14 to individual 10 in the event a power failure occurs.

Figure 4:
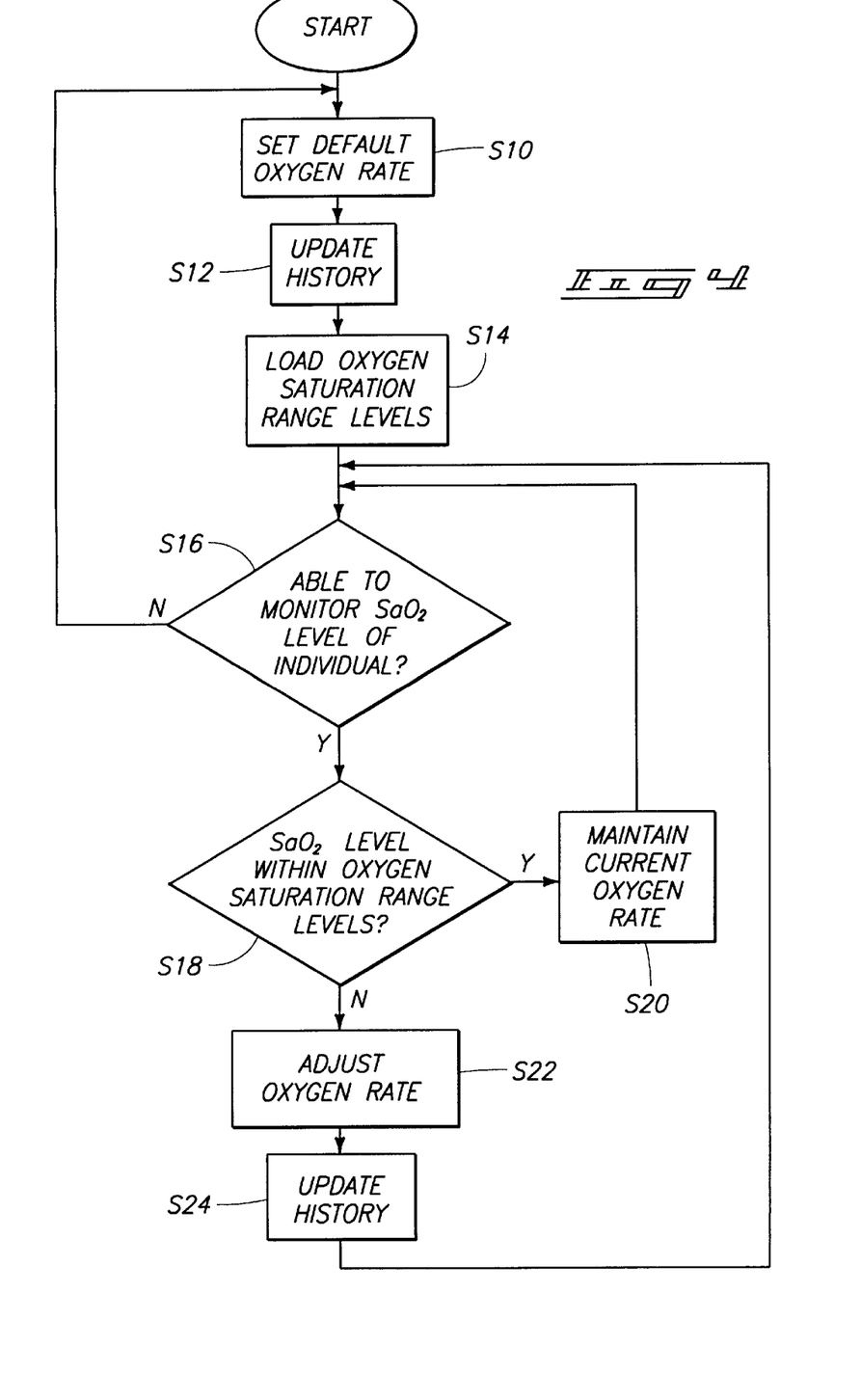
FIG. 4 is a flow chart illustrating an exemplary operation of the oximetry device.

Referring to FIG. 4, operations of oximetry device 12 in accordance with one embodiment are described. Initially at step SIO, microcontroller 50 instructs register 45 to input the default supplemental oxygen rate received from central computer 34 into memory 46. At step S12, microcontroller 50 instructs tri-state buffers 48, 49 to input saturation level information and quantity of supplemental oxygen information into memory 46 to update the history stored therein. Thereafter, microcontroller 50 is configured to load oxygen saturation range levels received form central computer 34 into memory 46 via register 45. Such range levels are typically prescribed by the physician.

At step S16, microcontroller 50 determines whether a saturation level measurement is obtained from oxygen saturation sensor 16. Responsive to no data being received from sensor 16, microcontroller 50 proceeds to step S10 to apply supplemental oxygen to individual 10 at the default oxygen rate. If sufficient oxygen saturation level information is obtained at step S16, microcontroller 50 proceeds to step S18 to determine whether the saturated oxygen level is within the oxygen saturation range levels inputted from the physician. If the measured saturation level of individual 10 is within the prescribed range, microcontroller 50 proceeds to step S20 to maintain the flow of supplemental oxygen from source 14 at the current rate. The history within memory 46 can be updated in step S20 in some embodiments.

If the read saturation level at step S18 is not within the prescribed saturation range, microcontroller 50 proceeds to step S22 to adjust flow valve 28 to either decrease or increase the flow of supplemental oxygen from source 14 to individual 10. Next, microcontroller 50 proceeds to step S24 to update the history within memory 46 to store the measured saturation level, the saturation range and the flow of supplemental oxygen to individual 10. Thereafter, microcontroller 50 proceeds to step S16 to continue to monitor saturation levels of the individual.

Figure 5:
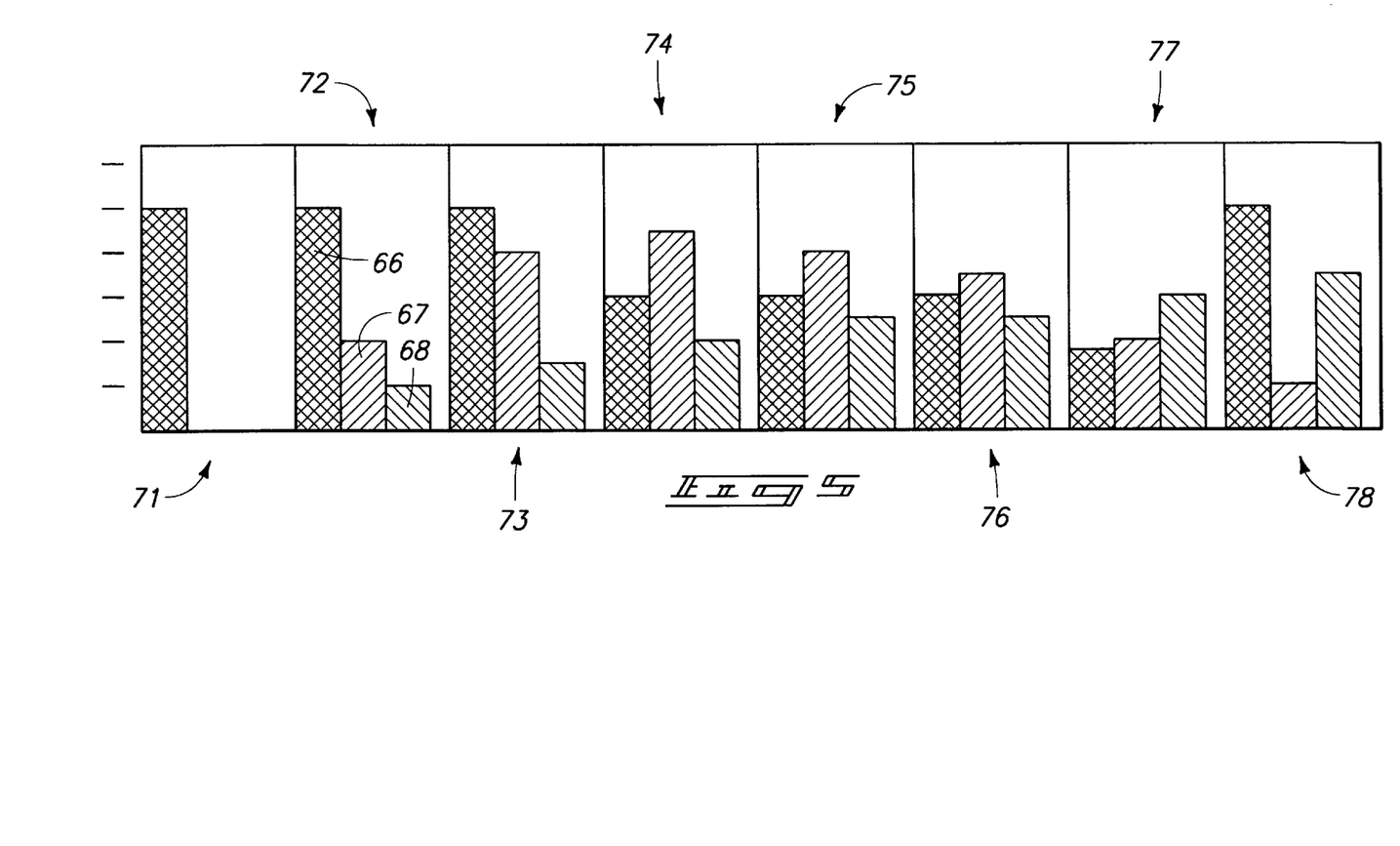
FIG. 5 is a graph illustrating oxygen saturation levels of an individual and supplemental oxygen flows.

Referring to FIG. 5, an exemplary history illustrating oxygen saturation levels and respective supplemental oxygen flows are depicted in a plurality of graphs 71–78. As previously mentioned, the history can be stored within memory 46 for subsequent communication to a physician.

Individual graphs 71–78 can include up to three bar indications corresponding to passage of time represented by bar 66, percentage of the patient's oxygen saturation being out-of-range represented by bar 67 and flow of supplemental oxygen supplied to individual 10 represented by bar 68. Respective increments for bars 66–68 shown on the left include minutes, percentage and oxygen flow in liters per minute. In one embodiment of the invention, incremental changes in the flow of supplemental oxygen occur in 0.5 liter per minute increments.

Graph 71 corresponds to a moment in time (e.g., five minutes from a previous change as indicated by bar 66) wherein the oxygen saturation is within a desired range of values as prescribed by a physician. An exemplary range of desired oxygen saturation percentage is 85–90 percent in the described embodiment. Other desired ranges are possible. No change is made to the flow of supplemental oxygen while the patient is within the desired oxygen saturation range.

Graph 72 corresponds to the oxygen saturation being outside of the desired range by approximately two percent as shown by bar 67. Oximetry device 12 is configured in the described embodiment to adjust the supplemental oxygen applied to individual 10 from source 14 at different times depending upon the oxygen saturation level of individual 10.

For example, in accordance with the described embodiment, oximetry device 10 is configured to adjust the flow of supplemental oxygen (i.e., either upward or downward) every five minutes if the individual's level is within a first deviate range, or approximately 4 percent of the desired saturation range. If the oxygen saturation level deviates within a second deviate range, such as more than 4 percent from the desired level, then oximetry device 12 is configured to adjust the flow of supplemental oxygen from source 14 to individual 10 every three minutes. The first and second deviate ranges, the desired range and the corresponding adjustment time periods may be varied dependent upon the particular application or patient's condition.

When the patient's oxygen saturation is within the desired range as prescribed by the physician, oximetry device 12 continues to monitor the level of the patient's oxygen saturation level at a given interval. In one embodiment, the given increment while the patient is within the desired range is five minutes. Other increments can be utilized for monitoring and adjusting the flow of supplemental oxygen to individual 10.

Still referring to graph 72, line 66 indicates an adjustment time of approximately five minutes while the patient's oxygen saturation level is within 4 percent of the desired range (e.g., within the first deviate range). Any change in flow of supplemental oxygen could occur as soon as the patient enters the first deviate range and every five minutes thereafter. The flow of supplemental oxygen is increased by an increment of 0.5 liters per minute at graph 72. With reference to FIG. 5, it is assumed that the oxygen saturation level of individual 10 is below the desired range and therefore additional oxygen is needed as shown by bar 68. It is also possible that the supplemental oxygen could be decreased if the oxygen saturation level were too high.

Referring to graph 73, the individual's oxygen saturation levels are again measured following five minutes as indicated by bar 66. As represented by bar 67, the person's percentage of oxygen saturation out-of-range is approximately five percent (i.e., within the second deviate range).

When the out-of-range percentage exceeds a predetermined number such as four percent, oximetry device 12 is preferably configured to monitor the person's oxygen saturation level at increased increments such as three minutes. Because the person's oxygen saturation level is still out of the desired range (i.e., their oxygen saturation level is low as represented by graphs 72, 73), the flow of supplemental oxygen is increased again by 0.5 liters per minute as represented by line 68.

At graph 74, oximetry device 12 monitors the person's oxygen saturation level following three minutes as represented by bar 66. The percentage of out-of-range of the oxygen saturation exceeds the desired amount by four percent. Therefore, oximetry device 12 measures the patient's oxygen saturation level following three minutes where it is determined that the range is still outside of the four percent as indicated by bar 67. Therefore, the flow of supplemental oxygen is increased to 1.5 liters per minute as represented by bar 68.

Referring to graph 76, the oxygen saturation level of the individual is within the first deviate range as represented by bar 67 and therefore no adjustment is made to the flow of supplemental oxygen as represented by bar 68 at the moment of time of graph 76.

Referring to graph 77, oximetry device 12 waits two minutes following entry above the four percent out-of-range amount (i.e., within the first deviate range) corresponding to the five minute change rate protocol. Oximetry device increases supplemental oxygen flow to 2.5 liters per minute as represented by bar 68 in graph 77.

Referring to graph 78, the out-of-range oxygen saturation level of individual 10 is still within the first deviate range as shown by bar 67. Therefore, oximetry device 12 implements any change in supplemental oxygen at five minute intervals. Since the individual is still below the desired range, the supplemental oxygen flow rate is increased to three liters per minute as represented by bar 68 of graph 78. Such continues until the oxygen saturation level of individual 10 is within the desired range prescribed by the physician.

Figure 6:
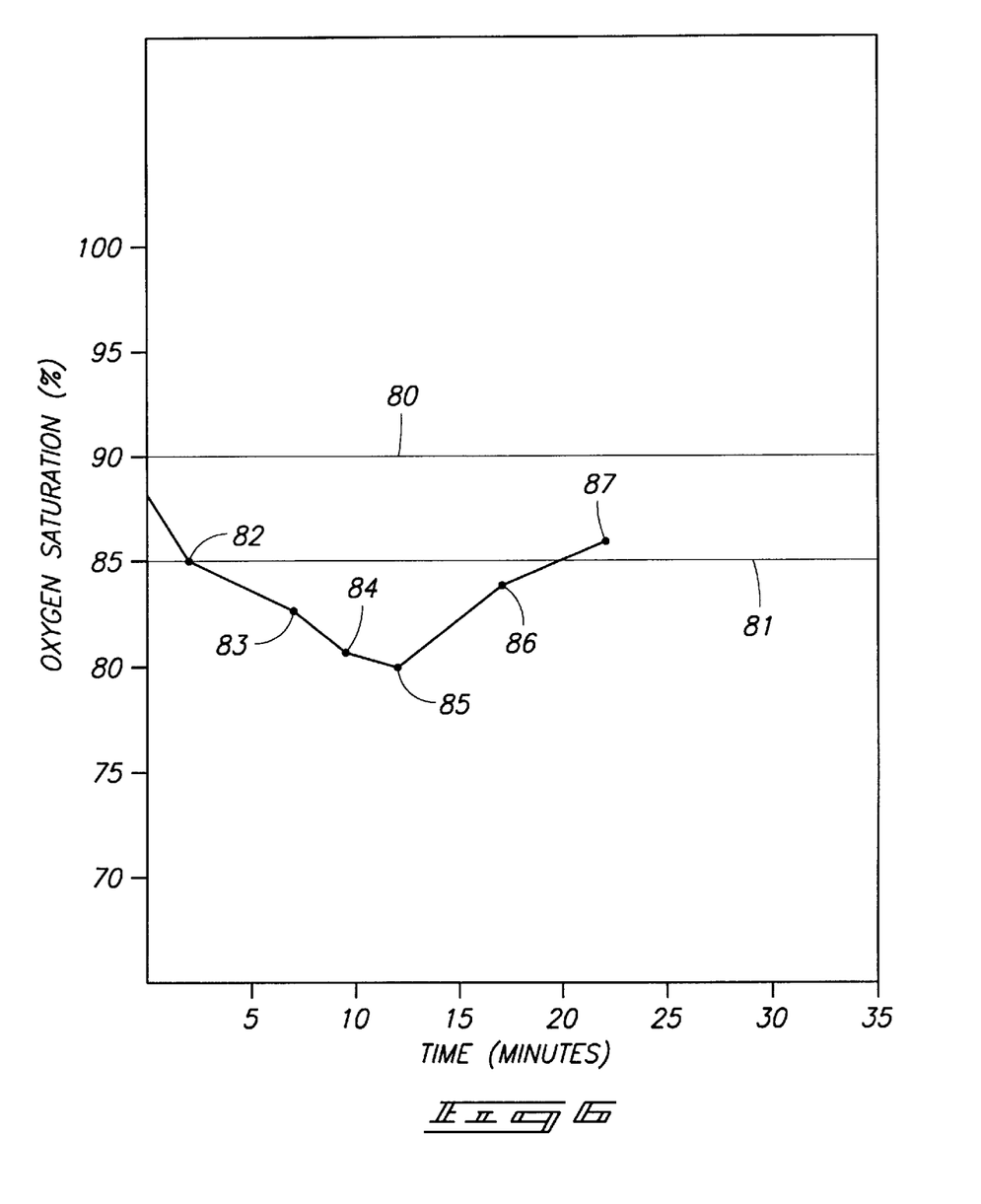
FIG. 6 is a graph illustrating oxygen saturation levels of an individual over a period of time.

Referring to FIG. 6, a history of oxygen saturation values is plotted against time responsive to monitoring and adjustment of supplemental oxygen flow to individual 10 by oximetry device 12. The desired oxygen saturation range of individual 10 is depicted by minimum saturation level line 81 corresponding to 85% oxygen saturation and maximum saturation level line 80 corresponding to 90% oxygen saturation.

During approximately the first two minutes, the oxygen saturation level of individual 10 is within the desired range. At point 82, corresponding to approximately two minutes, the oxygen saturation level of individual 10 drops below minimum value 81. The flow of supplemental oxygen is preferably increased at point 82. However, the oxygen saturation level of individual 10 has not dropped to the second deviate range (i.e., approximately four percent out-of-range). Therefore, any change in supplemental oxygen flow is implemented at five minute intervals.

At point 83, approximately five minutes following point 82, oximetry device 12 again increases the flow of supplemental oxygen to individual 10 inasmuch as individual 10 is still out of the desired oxygen saturation range.

At point 84, it is determined that the individual has exceeded the excessive four percent range (i.e., the oxygen saturation level of the individual has entered the second deviate range). Therefore, the supplemental oxygen flow level is increased again. Additional changes in supplemental oxygen delivered to individual 10 thereafter occur at three minute intervals (e.g., corresponding to point 85). The three minute interval is utilized as long as the oxygen saturation level is within the second deviate range. The supplemental oxygen flow is increased at point 85 in an attempt to raise the individual's oxygen saturation level.

Once the level is above the four percent out-of-range level or within the first deviate range, any change occurs five minutes following the previous change corresponding to point 86. Because the individual is still below the desired range at point 86, the flow of supplemental oxygen can be increased again until the patient is brought within the desired range indicated by point 87.

The oxygen saturation level and corresponding supplemental oxygen flow levels may be stored in memory 46 to provide a history. The history data can comprise data at selected points 82–87, or alternatively, continuous data while device 12 is in operation. In another configuration, oximetry device 12 is configured to only store out of range occurrences such as points 83–86 to comprise history.

The exemplary history depicted in FIG. 6 can be stored within memory 46 of oximetry device 12 and downloaded to central computer 34 by the physician for remote monitoring of the individual. In addition, oximetry device 12 can be configured to output an alarm to the physician if a predetermined number of out-of-range occurrences happen, or alternatively if one occurrence lasts for a predetermined length of time.

If at any time a supplemental oxygen flow change results in an out-of-range value being determined in the opposite direction that initially caused the change in flow, then the flow from supplemental oxygen source 14 is reset to the prior setting before the initial change in oxygen flow was made. Such attempts to return individual 10 to the desired oxygen saturation level range.

Once the individual returns to the desired range as indicated at point 87, oximetry device 12 can return to the default setting of supplying supplemental oxygen to individual 10. A default flow rate of supplemental oxygen can be within zero to six liters per minute in the described embodiment. Other flow rates of supplemental oxygen can be utilized depending upon the particular circumstances of patient 10.

Memory 46 of oximetry device 12 is preferably configured to store data for an extended period of time such as days or weeks in the described embodiment. Such can comprise continuous information relating to the oxygen saturation level of individual 10 and corresponding flows of supplemental oxygen from source 14. Continuous data can include both data within and outside of the desired oxygen saturation range for individual 10.

As previously mentioned, device 12 can be configured to only store out-of-range data within memory 46. Such could also be configured to monitor the number of occurrences wherein the oxygen saturation level of the individual is out of the desired range prescribed by the physician. In such an event, oximetry device 12 could output an alarm to central computer 34 to notify the physician of numerous out-of-range occurrences of individual 10.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. An oximetry device comprising:
    an oxygen saturation sensor adapted to couple with an individual and configured to provide oxygen saturation information of the individual;
    an oxygen flow sensor adapted to couple with an oxygen source and configured to provide flow rate information of supplemental oxygen delivered to the individual;
    a controller coupled with the oxygen saturation sensor and adapted to control a flow valve to control the flow rate of supplemental oxygen delivered to the individual responsive to the oxygen saturation information provided by the oxygen saturation sensor; and
    a memory device coupled with the controller and configured to store the oxygen saturation information and flow rate information of supplemental oxygen.

2. The oximetry device according to claim 1 wherein the memory device is configured to store a history including the oxygen saturation information comprising a plurality of oxygen saturation levels and the flow rate information comprising a plurality of supplemental oxygen flow rate values corresponding to the respective oxygen saturation levels.

3. The oximetry device according to claim 1 wherein the memory is configured to store a desired oxygen saturation range.

4. The oximetry device according to claim 3 wherein the controller is configured to adjust the flow rate of supplemental oxygen delivered to the individual responsive to the oxygen saturation information being out of the desired oxygen saturation range.

5. The oximetry device according to claim 1 further comprising an interface coupled with the memory and adapted to couple with an external data device, the interface being configured to communicate the oxygen saturation information and corresponding supplemental oxygen flow rate information to the external data device.

6. The oximetry device according to claim 5 wherein the interface is configured to receive a desired oxygen saturation range from the external data device.

7. The oximetry device according to claim 5 wherein the interface is configured to communicate a history including the oxygen saturation information comprising a plurality of oxygen saturation levels and the flow rate information comprising a plurality of supplemental oxygen flow rate values corresponding to the respective oxygen saturation levels to the external data device, and receive a desired saturation range from the external data device.

8. The oximetry device according to claim 5 wherein the interface is configured to communicate via a telephone network.

9. The oximetry device according to claim 1 wherein the controller is configured to selectively deliver supplemental oxygen to the individual at a default flow rate.

10. The oximetry device according to claim 1 wherein the oximetry device is configured for use within an open oxygen delivery system.

11. An open oxygen delivery system oximetry device comprising:
    an oxygen saturation sensor adapted to couple with an individual and provide oxygen saturation information of the individual;
    an oxygen flow sensor adapted to couple with an oxygen source and provide flow rate information of supplemental oxygen delivered to the individual;
    a controller coupled with the oxygen saturation sensor and the oxygen flow sensor, the controller being adapted to control a flow valve to control the flow rate of supplemental oxygen delivered to the individual responsive to the oxygen saturation information provided by the oxygen saturation sensor, the controller being further adapted to selectively control the flow valve to deliver oxygen to the individual at a predefined default rate;
    a memory device coupled with the controller and configured to store a history including the oxygen saturation information comprising a plurality of saturation levels measured over a period of time and the flow rate information comprising a plurality of supplemental oxygen flow rate values corresponding to the respective oxygen saturation levels; and
    an interface coupled with the memory and adapted to couple with an external data device, the interface being configured to communicate the history to the external data device and receive a desired oxygen saturation range from the external data device.

12. An oxygen saturation control method comprising:
    providing an oxygen source;
    coupling an individual with the oxygen source;
    obtaining oxygen saturation information of the individual;
    selectively delivering a quantity of supplemental oxygen at a flow rate to the individual from the oxygen source responsive to the obtaining; and
    storing the oxygen saturation information of the individual and flow rate information of the supplemental oxygen delivered to the individual.

13. The method according to claim 12 further comprising communicating the oxygen saturation information and the supplemental oxygen flow rate information to an external data device.

14. The method according to claim 12 further comprising storing a desired oxygen saturation range.

15. The method according to claim 14 further comprising:
    comparing the oxygen saturation information with the desired oxygen saturation range; and
    adjusting the flow rate of supplemental oxygen delivered to the individual responsive to the comparing.

16. The method according to claim 14 wherein the storing the oxygen saturation information and flow rate information is responsive to the oxygen saturation level of the individual being outside of the desired saturation range.

17. The method according to claim 12 wherein the storing comprises storing a history including oxygen saturation information comprising a plurality of oxygen saturation levels and flow rate information comprising a plurality of supplemental oxygen flow rate values corresponding to the respective oxygen saturation levels.

18. The method according to claim 17 further comprising communicating the history to an external data device.

19. The method according to claim 17 further comprising selectively delivering oxygen at a default flow rate to the individual.

20. The method according to claim 12 wherein the control method comprises a control method of an open oxygen delivery system.

* * * * *